United States Patent [19]

Chagnon et al.

[11] Patent Number: 5,935,866
[45] Date of Patent: Aug. 10, 1999

[54] PREPARATION OF SUB 100 A MAGNETIC PARTICLES AND MAGNETIC MOLECULAR SWITCHES

[75] Inventors: Mark S. Chagnon, Pelham, N.H.; John R. Ferris, Newburyport, Mass.; Michelle J. Carter, Derry, N.H.; Tracy J. Hamilton, Hudson, N.H.; Maria A. Gray, Derry, N.H.

[73] Assignee: Binax NH, Inc., Atkinson, N.H.

[21] Appl. No.: 07/894,260

[22] Filed: Jun. 8, 1992

Related U.S. Application Data

[63] Continuation-in-part of application No. 07/556,169, Aug. 10, 1990, abandoned, which is a continuation-in-part of application No. 07/455,071, Dec. 22, 1989, abandoned.

[51] Int. Cl.⁶ ............ G01N 33/553; C12Q 1/68; C07F 7/28; C01G 49/08
[52] U.S. Cl. ............ 436/526; 435/6; 556/52; 556/56; 428/407; 427/216; 252/62.51 R; 252/62.51 C; 252/62.56
[58] Field of Search .......... 252/62.51 R, 62.51 C, 252/62.56, 302, 313.1; 427/216; 428/407; 556/52, 56; 436/526; 435/6

[56] References Cited

U.S. PATENT DOCUMENTS

| | | | |
|---|---|---|---|
| 2,438,230 | 10/1948 | Ryznar | 252/313.1 |
| 3,888,788 | 6/1975 | Yates | 252/309 |
| 4,157,323 | 6/1979 | Yen et al. | 436/526 |
| 4,285,819 | 8/1981 | Yen et al. | 210/679 |
| 4,454,234 | 6/1984 | Czerlinski | 436/526 |
| 4,456,509 | 6/1984 | Habeeb et al. | 204/59 R |
| 4,554,088 | 11/1985 | Whitehead | 252/62.51 R |
| 4,578,195 | 3/1986 | Moore et al. | 210/679 |
| 4,632,904 | 12/1986 | Lee | 435/176 |
| 4,675,173 | 6/1987 | Widder | 436/526 |
| 4,945,049 | 7/1990 | Hamaya et al. | 435/168 |
| 5,071,076 | 12/1991 | Chagnon et al. | 241/21 |
| 5,108,933 | 4/1992 | Liberti et al. | 436/526 |
| 5,206,159 | 4/1993 | Cohen et al. | 435/792 |

FOREIGN PATENT DOCUMENTS

| | | | |
|---|---|---|---|
| 0125995 | 11/1984 | European Pat. Off. | G01N 33/54 |
| 0546939 | 6/1993 | European Pat. Off. | A61K 49/00 |
| 8706492 | 11/1987 | WIPO . | |
| 8911335 | 11/1989 | WIPO | B01J 13/02 |
| 9109678 | 7/1991 | WIPO | B03C 1/00 |

OTHER PUBLICATIONS

Selbin, J. "Complexes of Dithiobenzoic Acids. V. Observations on the Nature of the Molybdenum–Sulfur Bond in Tetrakis(dithiobenzoato)Molybdenum(IV) Complexes," Inorganica Chimica Acta 71:201–204 (1983).

Turkevich, J. Colloidal Gold Part I Historical . . . Gold Bull 18 (1985):86–91.

*Primary Examiner*—Michael P. Woodward
*Attorney, Agent, or Firm*—Hayes, Soloway, Hennessey, Grossman & Hage, P.C.

[57] ABSTRACT

Inorganic oxides of substantially uniform particle size distribution are prepared by contacting aqueous solutions of an inorganic salt and an inorganic base across a porous membrane wherein the membrane contains a plurality of pores which allows for precipitation of a substantially monodisbursed size inorganic oxide particles on one side of the membrane and precipitation of a salt of the corresponding base on a second side of the membrane.

69 Claims, 1 Drawing Sheet

FIG. 1

PREPARATION OF SUB 100 Å MAGNETIC PARTICLES AND MAGNETIC MOLECULAR SWITCHES

CROSS-REFERENCE TO RELATED APPLICATION

This application is a continuation-in-part of U.S. application Ser. No. 07/556,169, filed Aug. 10, 1990, now abandoned, which is a continuation-in-part of U.S. application Ser. No. 07/455,071, filed Dec. 22, 1989, now abandoned. Attention is also directed to commonly assigned, co-pending application, 07/706,478, filed Dec. 13, 1991, and commonly assigned U.S. Pat. No. 5,071,076, the disclosures of which are incorporated by reference.

FIELD OF THE INVENTION

This invention relates to a method for producing inorganic oxides of substantially uniform particle size distribution, coating said particles with various functional moieties, and clustering said moieties together via controllably degradable chemical, complex, or ionic bonds. More particularly, this invention relates to a method of producing magnetic inorganic oxide particles of substantially uniform size, or organic coated particle beads, linking the particle or particle bead together to form a large aggregate cluster with different chemical, physical, or magnetic properties than the unit particle or bead, and controllably and predictably revising the cluster back to unit bead or particle size and vice versa.

BACKGROUND OF THE INVENTION

Separations of all types are routinely done by the exploitation of physical and chemical differences in the various species to be separated. Size exclusion, boiling point, and chemical affinity are techniques that have been used for separations of particles, chemical species, and biological moieties for hundreds of years. More recently, the use of magnetism has been used as a tool for separation of various species material from one another. By the early 1960's, the first stable magnetic fluid colloid had been described. Later research led to the development of a separations device based on magnetic density gradients in magnetic fluid columns. By 1979, magnetic particles coated with appropriate functional chemical groups for affinity chromatography separations were reported. The first commercial application of magnetic separations was described by Chagnon et al in U.S. Pat. No. 4,628,037. The Chagnon patent describes the use of amine terminated silane coupled magnetic particles for immunodiagnostic applications. The materials described in the Chagnon et al patent are now used commercially in medical diagnostic kits.

Magnetic separations have not been exclusively applied to in vitro applications. The use of magnetic separations for in vivo applications is becoming increasingly more accepted and important as a therapeutic and diagnostic tool. By the early 1980's, published reports described the magnetic targeting and isolation of chemotherapeutic drugs into rat-tail sarcoma. Widder (U.S. Pat. Nos. 4,849,210; 4,247,406; and 4,230,685) describe the use of magnetic albumin spheres for ultrasound contrast media and magnetic drug targeting. Schroeder (U.S. Pat. No. 4,501,726) reports a method of preparing magnetic starch beads for use in MRI imaging for the separation of $T_1/T_2$ relaxation signals.

In all of this previous work, the use of magnetic separations has been done on magnetic particles of varying particle size distribution. The magnetic particle is coated with an organic compound, and used either as a signal (e.g., MRI), targeting agent (e.g. in drug delivery) or for separation in a magnetic field (e.g. in vitro separations). However, an advantage in enhanced separations, for example, could be achieved if the magnetic particle could alter its size, shape or magnetic properties while in use in a controlled fashion.

Various methods have been reported for preparing inorganic or inorganic oxide particles of some degree of particle size control:

U.S. Pat. No. 5,071,076 describes a method for producing magnetic microparticles from metallocenes. The method involves combining an aqueous slurry of the metallocene and an aqueous slurry of a metal hydroxide and milling the slurries together.

U.S. Pat. No. 4,987,012 describes a process for preparing spherical particles of hydroxide having a particle diameter from 0.1 to 10 .mu.m by adding a corresponding metal alkoxide to a dispersion of a water-alcohol system having dispersed therein a metal oxide or hydroxide as a seed, under alkaline conditions and allowing a decomposition product from said metal alkoxide to attach onto said seed to effect particle growth of the seed. The improvement reported comprises maintaining said dispersion at a substantially constant pH within the range between 10 and 13 during the addition of the metal alkoxide to said dispersion and the subsequent particle growth of the seed, thereby to prepare mono-dispersed particles substantially free from particle aggregation having a sharp particle size distribution of a standard deviation of not greater than 0.5.

U.S. Pat. No. 4,985,273 describes a method of producing fine inorganic particles. The method comprises the steps of reacting an inorganic fine particle on the entire surface thereof with a silane type surface active agent containing a straight hydrocarbon chain and a functional group to form a monomolecular film on the entire surface of said inorganic fine particle, thereafter making the inorganic fine particles covered with the monomolecular film in a predetermined density on a substrate, and thereafter subjecting the monomolecular film to physical or chemical treatment to allow the functional groups to be chemically bonded to each other.

U.S. Pat. No. 4,945,049, reports on a method for preparing magnetic powder comprising homogeneous and fine particles using an alkali-producing enzyme. Particles having a particle size ranging from 50 to 500 nm's were reported.

U.S. Pat. No. 4,702,775 describes the control of particle size in the preparation of magnetite pigments. The mean particle size was brought to a value within the range of 0.06 to 0.5 .mu.m by means of a residence stage between the precipitation stage and the oxidation stage.

Various other disclosures describe the preparation of microporous membranes, primarily for a filtration purpose, which limit the passage of selected size molecules within a particular liquid medium. For example, U.S. Pat. No. 4,943,374 concerns the use of a microporous membrane constructed of a polyether sulfone and hydrophilization agent having a pore size which is within the range of 0.1 and 1.2 microns for the filtration of beer. U.S. Pat. No. 4,954,381 describes the preparation of porous substrates having well defined morphology. U.S. Pat. No. 4,964,992 describes a membrane filter having predetermined controlled porosity and to the method for making such a membrane filter. U.S. Pat. No. 5,057,226 describes a method of removing a constituent of a biological fluid including a blood component, said method including flowing the biological fluid past one side of a first semipermeable membrane, flowing solution containing a first precipitation agent past a second side of the membrane so as to cause transfer of the precipitation agent through the membrane to the biological fluid so as to improve precipitation characteristics of the fluid; and precipitating the constituent.

What emerges from the above, therefore, is the lack of a convenient method to control inorganic oxide particle size, such that particle size control can then be further utilized to manufacture novel aggregate particle clusters with unique chemical or physical-chemical properties.

Accordingly, it is an object of this invention to provide a method for producing inorganic oxides of substantially uniform particle size, coating said particles with various functional moieties, and clustering said moieties together via controllably degradable chemical, complex or ionic bonds.

It is also an object of this invention to provide a method of producing magnetic particle or organic coated particle beads, linking said particle or particle beads together to form a large aggregate cluster with different chemical, physical, or magnetic properties than the unit particle or bead from which it is derived, and controllably and predictably revising the cluster back to unit bead or particle, and vice versa.

It is also a further object of this invention to provide a method of producing unit magnetic crystals of small, substantially uniform particle size for use in preparing magnetic-molecular switches and apply such to several in vitro and in vivo medical and biological applications.

NOMENCLATURE

The term "magnetic crystal" is defined as a particle 10A to 10,000 A in diameter comprised of iron oxide, iron metal, cobalt metal, nickel metal, magnetic ferrites, magnetic alloys, or mixed lattice magnetic metals or metal oxides. The term "magnetic bead" is defined as a magnetic crystal or population of crystals coated by an organic moiety or polymer or inorganic moiety or polymer to form a bead of 10A to 500,000 A in diameter. The term "magneto-molecular switch" is defined as a cluster of magnetic crystals or beads formed by the attachment of organic moieties to the surface of the crystal or beads that link the beads or crystals together via controllably degradable chemical, complex, or ionic bonds.

SUMMARY OF THE INVENTION

This invention provides a method for preparing novel precipitated inorganic oxide crystal particles of substantially uniform particle size distribution. The method comprises contacting aqueous solutions of an inorganic salt and an inorganic base across a porous membrane wherein the membrane contains a plurality of pores which allows for precipitation of substantially mono-dispersed inorganic oxide particles on one side of the membrane and precipitation of a salt of the corresponding base on a second side of the membrane.

When the inorganic oxide crystal particles produced according to this method is an iron oxide particle of reduced particle size (e.g. $Fe_3O_4$), which are non-magnetic, they can be aggregated into one embodiment of the magneto-molecular switch which comprises attachment of organic moieties to the surface of the crystals that link the crystal together to from controllably degradable chemical, complex or ionic bonds. It has also been found that aggregate clusters of crystals can be prepared by air or inert gas drying of the crystal particles along with several different solution encapsulation techniques.

In a further embodiment of the magneto-molecular switch, the individual crystal particles or population of crystals so produced are coated by polymer encapsulation, adsorbtion of monomer followed by crosslinking, or by applying organo-metallic polymer coatings which are covalently bonded or adsorbed onto said particles, to form a non-reversibly coated bead of 10A to 500,000 A in diameter. Accordingly, the beads themselves can be aggregated into controllably degradable bead clusters by the organic moieties that may be present on the beads, or by further attachment of organic moieties to the bead surface, which in either case allow the beads to link together to form controllably degradable chemical, complex, or ionic bonds.

DETAILED DESCRIPTION OF A PREFERRED EMBODIMENT OF THE INVENTION

Description of the Sub 100A Ferrite Particle

Sub 100A ferrites have been prepared by the co-precipitation of metal(+2) and metal(+3) salts in aqueous solutions with aqueous base across a porous or dialysis membrane. The metal salt solutions are put into a dialysis bag and the bag is sealed. The bag containing the metal salt solution is then immersed in an aqueous solution of base (i.e. ammonium hydroxide) over a period of several minutes to several days, depending on the concentration of the various reactants, and a precipitate of metal oxide forms inside of the dialysis bag. The size of the particles thus prepared is controlled by: concentration of the metal salt solution; concentration of the base solution; pore size of the membrane; temperature of the various solutions; ionic strengths (or ionization constant) of solutions; and the contact times of each solution across the dialysis membrane.

It has further been discovered that metal oxide particles of various controlled size can also be formed by contacting an aqueous solution of metal salts with a dialysis bag filled with aqueous base. In this case, the desired metal oxide product will form outside of the dialysis bag.

Figure 1:
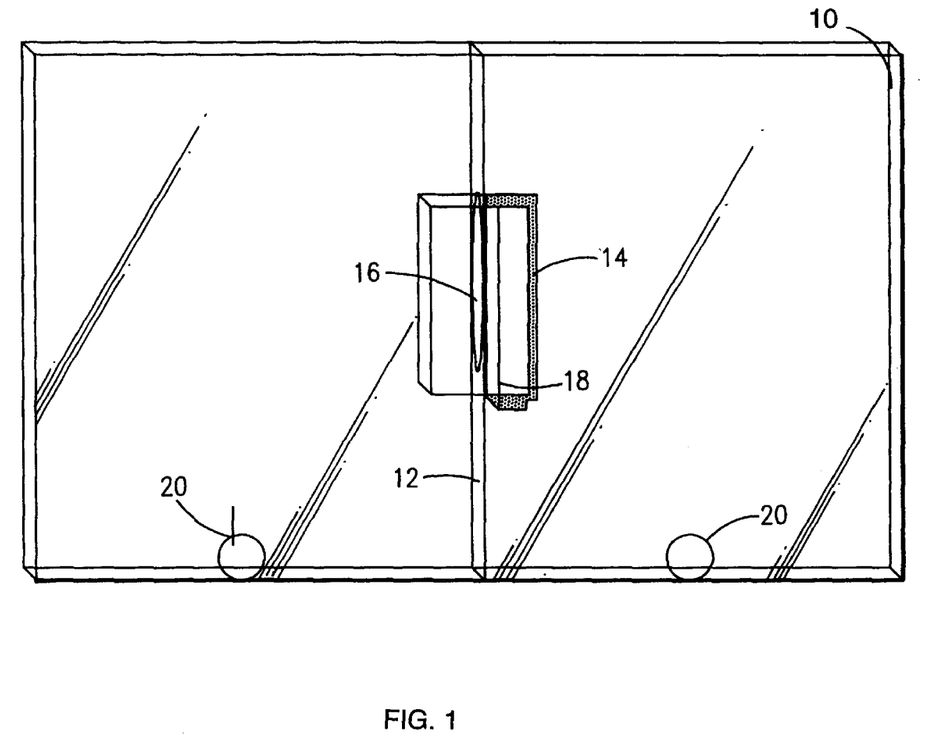
FIG. 1 is a drawing of a precipitation chamber used in accordance with the present invention.

In a preferred embodiment, the inorganic base and the inorganic salt solutions are maintained in large volume chambers separated by a porous membrane. Accordingly, large amounts of inorganic oxide of controlled particle size can be produced. As can be seen from FIG. 1, a large volume chamber (10) contains a partition (12), a semi-permeable membrane (14), an opening (16), a support (18) for mounting of the membrane, and portals (20) for draining. The metal salt solution is placed on the membrane side of the chamber, such that the metal oxide particles precipitate on that side of the large volume chamber.

It has also been discovered that the size of the cationic moiety on the base side of the membrane controls the size of the precipitated inorganic oxide particle so produced near the surface of the membrane within the inorganic salt solution. Apparently, the speed of dissociation of the inorganic base is believed to be controlled by the size of the cationic moiety; the larger the cationic moiety the slower the dissociation to cationic and anionic component. When the dissociation is relatively slow, a relatively low concentration of anionic moiety is present, providing a relatively low concentration of anion diffusing across the porous membrane and into the inorganic salt solution. Accordingly, the cationic component (of the inorganic salt) exists in large excess, thereby surrounding the slowly diffusing anion, resulting in precipitation of many small-sized inorganic oxide particles.

By contrast, if the cationic moiety of the inorganic base is relatively small, the speed of dissociation is relatively fast, providing a relatively large concentration of anionic moiety diffusing across the porous membrane and into the inorganic salt solution. At the surface of the membrane within the inorganic salt solution the cationic component (of the inorganic salt) once again exists in large excess. Accordingly, while the cationic component surrounds those anionic moieties which have diffused across the membrane, the elevated concentration of diffusing anionic moiety rapidly finds its way to the cationic surface of such a growing particle, so that a further layer of ionic bonding can result, thereby producing larger overall particle size prior to precipitation from solution.

It has been found, for example, that KOH in contact with an aqueous solution of $FeCl_2/FeCl_3$ affords iron oxide particles ($Fe_3O_4$) that are smaller in size as compared to iron oxide particles produced when LiOH is employed as the inorganic base. This would comport with the above insofar as the K+ ion is known to be relatively larger than the Li+ ion.

With respect to the foregoing, $NH_4OH$, KOH, LiOH, NaOH and other hydroxides formed by elements in group Ia of the periodic table serve as suitable inorganic base compounds. Inorganic salt solutions based on mixtures of the type $M^{(+3)}Y/M^{(+2)}Y$ include those wherein Y is selected from the group consisting of Cl, Br, I, $SO_4$, $NO_3$ and $PO_4$. M can be selected from the group consisting of Fe, Co, Ni, Zn, Mn, Mg, Ca, Ba, Sr, Cd, Hg, Al, B, Sc, Ga, V and In. The preferred inorganic salts are those which are readily productive in an aqueous medium of an anion and a cation which can combine with the aforementioned diffusing hydroxide anion to form an inorganic oxide.

Accordingly, inorganic oxide particles of the formula $M_3O_4$ are prepared wherein M is selected from the group consisting of Fe, Co, Ni, Zn, Mn, Hg, Ca, Ba, Sr, Cd, Hg, Al, B, Sc, Ga, V and In and mixtures thereof. It will also be appreciated that for a given $M_3O_4$ particle, the metal (M) may often be a combination of different oxidation states of the same metal component. For example, and in the preferred embodiments, $Fe_3O_4$ particles are prepared and represent a mixed Fe(+2)Fe(+3) oxide of the formula [Fe(+2)][Fe(+3)]$_2O_4$.

With respect to the foregoing, reference is made to the following:

I. The Effect of Alternative Base Counter Ions

The effect of alternative base counter ions on crystal properties such as size, distribution, magnetics, etc. was established as follows: Three experiments were conducted. All experimental conditions were identical except for the type of base. Experiment A utilizes NaOH, B with LiOH and C with KOH. For each experiment: 1. Wash a Spectra/Por®5 dialysis membrane (cellulose ester based membrane available from Spectrum Medical Industries, Inc.) and secure over the opening in the dialysis chamber; 2. Fill both sides of the tank with 20 liters of distilled $H_2O$ (at room temperature); 3. Dissolve 12.5 g $FeCl_2.4H_2O$ in 2 liters of distilled $H_2O$. Add 20 g $FeCl_3$ and stir until dissolved; 4. Decant all iron solution into the membrane side of chamber; 5. For A dissolve 55 g NaOH in 2 liters of distilled $H_2O$. For B dissolve 55 g LiOH in 2 liters of distilled $H_2O$. For C dissolve 60.6 g KOH in 2 liters of distilled $H_2O$. Decant base solution into opposite side of dialysis chamber. After 70 hours contact time, remove the crystal precipitate solution for evaluation. The results are listed below in Table 1.

TABLE 1

| Sample | Base Ion | Crystal Size(A) | Cluster Size(A) | Magnetics (Gauss) | Iron Conc. (mg/ml) | % Total Solids |
|---|---|---|---|---|---|---|
| A | Na | 60–80 | 300 | 340 | 7.0 | 1 |
| B | Li | 120–140 | 170–250 | 275 | 6.44 | 1 |
| C | K | 40 | 500 | 187 | 6.10 | 1 |

II. The Effect of Base Concentration

The effect of base concentration on crystal properties such as size, distribution, magnetic response, etc. was established as follows: Two experiments were conducted. All experimental conditions were identical except for base concentration. Experiment A was conducted at 0.5% NaOH. Experiment B was conducted at 0.25% NaOH. For each experiment: 1. Wash a SPECTRO/POR®5 dialysis membrane and secure over the opening in the dialysis chamber; 2. Fill both sides of the tank with 20 liters of $H_2O$ (at room temperature); 3. Dissolve 12.5 g $FeCl_2.4H_2O$ in 2 liters of distilled $H_2O$. Add 20 g $FeCl_3$ and stir until dissolved; 4. Decant all iron solution into the membrane side of chamber; 5. For concentration A: Dissolve 120 g NaOH in 2 liters distilled $H_2O$. Decant into opposite side of tank; For concentration B: Dissolve 55 g NaOH in 2 liters distilled $H_2O$. Decant into opposite side of tank; 6. After 70–80 hours contact time remove iron solution and precipitated crystals for evaluation. The results are listed below in Table 2.

TABLE 2

| Sample | Crystal Size(A) | Cluster Size(A) | Magnetics Gauss | Iron Conc. | % Total Solids |
|---|---|---|---|---|---|
| A | 70–80 | 500 | 360 | 7.0 mg/ml | 1.0 |
| B | 60–80 | 300 | 340 | 0.39 mg/ml | 0.085 |

It has also been found that the size of the particles may be effected by the following additional variable: the temperature of the solutions; whether the particles formed are removed (including magnetic removal, if the particles are of the appropriate size) from the immediate surface of the membrane; the pore size of the membrane; and whether or not the solutions are stirred. With respect to the pore size, membranes of different molecular-weight cut-offs (MWCO) have been examined. The MWCO represents a limit on the size of the molecule allowed to pass through the pore. MWCO's between 1000 and 500,000 have been investigated. The smaller the MWCO, the smaller the inorganic oxide produced.

Description of Magnetic Clusters

Iron oxide, for example, has been prepared using this technique in sizes of 80A, 50A and 20A, all with a narrow (+/−10%) particle size distribution. A product that agrees with x-ray diffraction patterns for $Fe_3O_4$ has been prepared in 100, 80, 50 and 20A crystal sizes. The supra 50A particles of $Fe_3O_4$ have domain magnetization, when measured by a Vibrating Sample Magnetometer (VSM), of 5660 gauss. This result is in agreement with the literature. The sub 50A $Fe_3O_4$ crystals surprisingly have a very low magnetization. In fact, crystals of 20A $Fe_3O_4$ have domain magnetization of less than 100 gauss. This low magnetization observed in sub 50A $Fe_3O_4$ crystals is likely the result of having insufficient mass for spin coupling and the absence of domain wall formation.

Surprisingly, when non-magnetic sub 50A crystals of $Fe_3O_4$ are clustered together to form aggregates of 250A or greater, the aggregate particles are strongly magnetic. Aggregate particles of 500A or greater in diameter, when measured by VSM, have domain magnetizations in excess of 4000 gauss.

It has been further discovered that if the aggregates of magnetic crystals are returned to non-aggregated unit sub 50A crystal size, the effect if reversed, that is, the magnetization is returned to nominally 0.

The exact size at which the onset of superparamagnetic behavior occurs in the unit crystal, is a function of the crystal structure, shape, and composition.

Several different cubic ferrites have been prepared with several different crystal sizes each. The onset of superparamagnetic behavior occurs at various size unit crystals depending on the exact composition. Table 3 is an estimate of the size where supermagnetic behavior begins for several different crystal compositions.

TABLE 3

| MINIMUM SIZE FOR CRYSTAL COMPOSITION | SUPERPARAMAGNETIZATION |
|---|---|
| $Fe_3O_4$ | 50 A |
| $Fe_{2.5}Zn_{0.5}O_4$ | 80 A |
| $Fe_2ZnO_4$ | 120 A |
| $Fe_{2.5}Mn_{0.5}O_4$ | 100 A |
| $Fe_2MnO_4$ | 50 A |
| $Fe_2Sr_{0.25}Al_{0.5}O_4$ | 20 A |

The substantially uniform size $Fe_3O_4$ affords a crystal lattice which contains primarily trivalent iron (Fe+3) at or near the surface of the crystal. It has been found that these "surface trivalent" elements of the lattice contain imperfections which make them available for direct covalent attachment of the organometallic compounds of the formula $Ti(OR)_4$ according to the following general equation:

It should be noted that the imperfections of the surface trivalent iron is somewhat short-lived, and if organo-metallic coating is delayed, oxidation can occur causing the development of surface hydroxyls, which can hydrolyze, to provide an FeO coating, precluding direct covalent attachment of the organo-metallic moiety. For example, freshly made $Fe_3O_4$ will spontaneously react; $Fe_3O_4$ material after 24 hours reacts but requires about 1 hour of dwell time; after 48 hours the coupling reaction takes place very slowly and is generally incomplete.

Organo-metallic compounds are preferably of the formula $Ti(OR)_4$ wherein R is an alkyl group and the dissociation to the reactive component follows the following general reaction criterion:

Accordingly, $R_1$, $R_2$, $R_3$ and $R_4$ are selected so that rapid dissociation of the first radical ($R_1$) is fast, and dissociation of subsequent radicals ($R_2$–$R_4$) is slow. It has been found that when the radicals $R_1$–$R_4$ are collectively alkyl type, the dissociation is linear with respect to the length of the chain (the shorter the chain, the faster the dissociation). Therefore, it is possible to shift the reactivity of such organo-metallic compounds by simply replacing shorter alkyl substituents with longer alkyl substitution. It has also been found that when R is an aryl moiety, dissociation is relatively slow. Other moieties (e.g. esters, ketones) have been found to provide intermediate dissociation constants.

Description of Chemical Bond Magneto Clusters

Aggregate clusters of sub 50A non-magnetic ferrites were prepared by several techniques including air drying of the particles to form agglomerates, argon drying at room temperature, several different solution encapsulation techniques and by covalent coupling of surface modified crystals. All of the techniques employed provided particle clusters of at least 250A diameter and mostly of 500A or greater. In all cases, surprisingly, the particle clusters of non-magnetic ferrite crystal were magnetic.

Organo-metallic coating with monomer material capable of adsorptive or covalent binding to iron oxide particles (of less controlled particle size) is reported in the co-pending parent application 556,169, filed Aug. 10, 1990. According to the instant invention, such coatings can now advantageously be applied to inorganic oxide crystal particles of substantially uniform particle size distribution. For example, substantially uniform sub 50A $Fe_3O_4$ was treated with titanium tetra-isopropoxide and subsequently terminated with a C-6 carboxylic acid and a second population was terminated with a C-6 amine. When mixed together and measured for magnetic response, no magnetic moment was observed. However, upon addition of methyl diisocyanate, the amine and carboxyl terminus groups spontaneously caused clustered aggregates of magnetic particles to form and a magnetic moment proportional to the concentration of methyl diisocyanate added was observed until saturations occurred when all of the amine and/or carboxyl reagent was exhausted.

Description of the Magnetic Molecular Switch

Another application for the magnetic cluster is the so-called magneto-molecular switches. Sub 50A non-magnetic $Fe_3O_4$ particles are treated by mixing them in a non-aqueous solvent, such as dimethyl formamide and with titanium tri-isopropoxy-3,4-dihyroxy phenoxide.

The particles prepared in this fashion, are titanium oxide coated with o-dihyroxy benzene termination and are non-magnetic in an applied field. Upon addition of a solution of a transition metal, sodium molybdate and tungsten, for example, a 2:1 coordination complex forms between 1 metal clustered and 2 o-hydroxy benzene atoms causing the particles to become clustered and giving rise to a magnetic signal that is proportional to the concentration of metal ion coupling formed.

Surprisingly, a slight change in pH causes the complex to decompose and the resulting magnetization return to 0. A return to the pH favorable for the formation of the complex results in a renewed magnetization of equivalent field strength to that achieved after initial addition of metalate ion. This so called magneto-molecular switch is useful for, but not limited to: magnetic tracers for in vitro analysis, magnetic tracers for in vivo diagnostics, magnetic processing by metals (especially for group VI transition metals), analysis of metals, filtering aids, magneto chromatography, and cell sorting.

Description of the Applications

The inorganic oxide crystal particles of substantially uniform particle size distribution may be coupled to biological or organic molecules with affinity for or the ability to adsorb or which interact with certain other biological or organic molecules. Particles so coupled may be used in a variety of in vitro or in vivo systems involving separation steps or the directed movement of coupled molecules to particular sites, including, but not limited to, immunological assays, other biological assays, biochemical or enzymatic reactions, affinity chromatographic purifications, cell sorting and diagnostic and therapeutic uses.

Magnetic In vitro Tracers

Controlled size inorganic oxide particles of this invention can be covalently bonded by conventional coupling chemistries to bioaffinity adsorbents including, but not limited to, antibodies (ligands, e.g., anti-thyroxine, anti-triiodothyronine, anti-thyroid stimulating hormone, anti-thyroid binding globulin, anti-thyroglobulin, anti-digoxin, anti-cortisol, anti-insulin, anti-theophylline, anti-vitamin B-12, anti-folate, anti-ferritin, anti-human chorionic gonadotropin, anti-follicle stimulating hormone, anti-progesterone, anti-testosterone, anti-estriol, anti-estradiol, anti-prolactin, anti-human placental lactogen, anti-gastrin and anti-human growth hormone antibodies), antigens (ligates, e.g. hormones, peptides, pharmacological agents, vitamins, cofactors, hematolgical substances, virus antigens, nucleic acids and nucleotides) and specific bonding proteins, which coupled particles can be used in immunoassays or other binding assays for the measurement of analytes in solution. In broad aspect, when such controlled size inorganic oxide particles are non-magnetic, and bound to a given species having specific affinity for a corresponding biochemical moiety, the magnetic response becomes directly proportional to the concentration of the biochemical moiety causing the complexation.

For example, crystals are prepared that are, as explained earlier, below the critical size for the development of super-paramagnetic behavior. The non-magnetic crystals are then coated with an organo-metallic coating, for example, amino-hexyl-titanium-tri-isopropoxide, and thermally crosslinked to form an organo-titanium polymer coating having an organic spacer arm (the hexyl moiety) and organic functional group (i.e., the amino-group). Anti-T-4 (thyroid hormone) with carboxylic acid terminal functionality is then coupled to the non-magnetic crystal in the presence of CDI (carbodimide catalyst) thereby forming an amide linkage between Anti-T-4 and the coated particle. Upon the addition of T-4 hormone, clusters are formed, and magnetic properties are detected.

In a further embodiment, an antibody, such as IgG, is coupled to the non-magnetic crystals, followed by addition of antitithiophillene. Upon addition of thiophillene, magnetic clusters are formed.

In vivo Tracers

A surface modification is put on the surface of non-magnetic $Fe_3O_4$. The modified reagent is injected into a patient and a complex is formed at a specific site in the body. The patient is imaged by MRI, or other suitable magnetic detection techniques.

Magnetic Metal Processing/Metal Analysis

Non-magnetic $Fe_3O_4$ is coupled to chelating agents and put into contact with the process stream. The complex forms and gives rise to a magnetic moment on the cluster thus formed. The cluster and metal of choice are collected with a magnet. The pH is changed to strip the metal and the product is collected. For example, the non-magnetic crystals are prepared as described above, with an organo-titanium polymer coating having an organic spacer arm and a terminal amino functionality. The particles are then reacted, by and through the amino functionality, with 2,3-dihydroxy-benzoic acid (upon addition of CDI) to form an amide coupled product with 2,3-dihydroxy-benzene termination. When such dihydroxy functionality is brought into contact with metals such as Tu, or Mo, under controlled pH (6–8) a complex forms and gives rise to the magnetic moment. In a similar manner, 2,3-dithiobenzoic acid can be employed, providing terminal dithio functionality, for more selective chelating with, e.g., Mo.

EXAMPLES

Example 1

PREPARATION OF 25A DIALYZED IRON OXIDE CRYSTAL

A stock of solution of iron salt is prepared by first dissolving 2.5 g $FeCl_2.H_2O$ (Aldrich) in 37.5 g of tap water at 65° C., then adding 4 g FeCl₃ (Aldrich) to the solution and mixing until dissolved. The solution is dark orange in color. From this stock solution a dilute solution is prepared for dialysis by adding 3 g of the stock iron solution to 297 g of warm (50° C.) water. 50 g of this 1% solution is sealed in cellulose dialysis tubing (Sigma MW12000) that has been prepared in the following manner:

A 12 inch strip of tubing is soaked in warm water for 30 minutes, rinsed thoroughly in warm water and stored in cool water until the addition of iron solution.

The dialysis tubing containing 50 g of the 1% iron solution is scaled and then placed in a 2% ammonium hydroxide solution:

6 g NH₄OH (Ashland Chemical 28–30%) in 294 g cool water

The container holding the NH₄OH solution and dialysis sack of iron solution is covered tightly and allowed to dialyze at room temperature until equilibrium is reached (4–6 hours). An orange precipitate of iron oxide forms inside the dialysis sack, white precipitate of ammonium chloride forms outside the sack. The precipitate is decanted from the tubing and washed by centrifuging, decanting the supernatant, and adding water. This step is repeated three times.

Example 2

PREPARATION OF 50A DIALYZED IRON OXIDE CRYSTAL

A stock of solution of iron salt is prepared by first dissolving 2.5 g FeCl₂.4H₂O (Aldrich) in 37.5 g of tap water at 65° C., then adding 4 g FeCl₃ (Aldrich) to the solution and mixing until dissolved. The solution is dark orange in color. From this stock solution a dilute solution is prepared for dialysis by adding 6 g of the stock iron solution to 295 g of warm (50° C.) water. 50 g of this 2% solution is sealed in cellulose dialysis tubing (Sigma MW12000) that has been prepared in the following manner:

A 12 inch strip of tubing is soaked in warm water for 30 minutes, rinsed thoroughly in warm water and stored in cool water until the addition of iron solution.

The dialysis tubing containing 50 g of the 2% iron solution is sealed and then placed in a 4% ammonium hydroxide solution:

12 g NH₄OH (Ashland Chemical 28–30%) in 288 g cool water

The container holding the NH₄OH solution and dialysis sack of iron solution is covered tightly and allowed to dialyze at room temperature until equilibrium is reached (4–6 hours). A dark orange precipitate of iron oxide forms inside the dialysis sack, white precipitate of ammonium chloride forms outside the sack. The precipitate is decanted from the tubing and washed by centrifuging, decanting the supernatant, and adding water. This step is repeated three times.

Example 3

PREPARATION OF 75A DIALYZED IRON OXIDE CRYSTAL

A stock solution of iron salt is prepared by first dissolving 2.5 g FeCl₂.4H₄O (Aldrich) in 37.5 g of tap water at 65° C., then adding 4 g FeCl₃ (Aldrich) to the solution and mixing until dissolved. The solution is dark orange in color. From this stock solution a dilute solution is prepared for dialysis by adding 9 g of the stock iron solution to 291 g of warm (50° C.) water. 50 g of this 3% solution is sealed in cellulose dialysis tubing (Sigma Mw12000) that has been prepared in the following manner:

A 12 inch strip of tubing is soaked in warm water for 30 minutes, rinsed thoroughly in warm water and stored in cool water until the addition of iron solution.

The dialysis tubing containing 50 g of the 3% iron solution is sealed and then placed in a 4% ammonium hydroxide solution:

12 g NH₄OH (Ashland Chemical 28–30%) in 288 g cool water

The container holding the NH₄OH solution and dialysis sack of iron solution is covered tightly and allowed to dialyze at room temperature until equilibrium is reached (4–6 hours). A brown precipitate of iron oxide forms inside the dialysis sack, while precipitate of ammonium chloride forms outside the sack. The precipitate is decanted from the tubing and washed by centrifuging, decanting the supernatant, and adding water. This step is repeated three times.

Example 4

SYNTHESIS OF TITANIUM COATED 100A MAGNETIC PARTICLES

Titanium coated magnetite, Fe₃O₄, is prepared using the following method:

Iron salts, FeCl₂.4H₂O and FeCl₃ (41 g) are each dissolved in 1000 cc of water. The solutions are combined into a 2 liter beaker and 70 ml of ammonium hydroxide is added while mixing. The beaker containing the resulting precipitate, 28 gm of Fe₃O₄, is then placed onto a permanent magnet to magnetically separate the magnetic precipitate from the salt by-products. After resting on the magnet for 5 minutes, the clear salt solution is decanted. The precipitate is then resuspended in a total of 1500 cc of water and placed on a permanent magnet for 5 minutes before decanting. The above washing process is repeated three additional times. After the final decanting, the magnetite is suspended in 1500 cc of dry acetone and magnetically separated as above. The particles are acetone washed a total of 3 times. After the final decanting, the particles are suspended in 500 cc of N,N dimethyl formamide.

The solution, 250 cc, is poured into a horizontal bead motor mill and milled for 10 minutes to ensure efficient dispersion. Titanium isopropoxide, 35 gm, dissolved in 50 cc of N,N dimethyl formamide is slowly pipetted into the funnel of the operating motormill and milled for 15 minutes.

The dispersion is removed from the mill, magnetically separated, decanted and water washed 5 times with 1000 cc of distilled water.

Example 5

SYNTHESIS OF TITANIUM COATED 20A NON MAGNETIC PARTICLES

This example illustrates the preparation of organometallic, titanium isopropoxide, coated non-magnetic 20A ferrites. A dispersion of non-magnetic 20A particles is water washed five times and anhydrous methanol washed three times by centrifugation. A total of 5.0 g of particle is suspended in 250 ml of N,N dimethyl formamide and milled in a bead motormill for 15 minutes. 12.0 g titanium isopropoxide dispersed in 30.0 g N,N-dimethyl formamide is slowly pipetted into the operating mill and milled for another 15 minutes. The product is then removed to form the mill and water washed five times by centrifugation and resuspended in distilled water.

Example 6

SYNTHESIS OF AMINE TERMINATED MAGNETIC PARTICLES

Magnetite coated with an organometallic, Ti, and terminated with a C-6 amine is prepared using the following method.

The precipitation, washing and coating with organometallic, titanium isopropoxide, is conducted in the exact manner as described above. After the washed magnetite particle, N,N-dimethyl formamide and titanium isoproxide have milled for 15 minutes, 15 gm of 6-amino 1-hexanol dissolved in 30 cc of N,N dimethyl formamide is pipetted into the operating mill. After milling for 15 minutes, the dispersion is heated for 20 minutes at 100° C. with occasional mixing. The dispersion is then allowed to cool, magnetically separated and washed five times with 1,000 cc of distilled water.

Example 7

SYNTHESIS OF CARBOXYL TERMINATED MAGNETIC PARTICLES

Magnetite coated with an organometallic, Ti, and terminated with a $C_6$ carboxyl group is prepared as follows:

14.2 g of 4-hydroxy butyric acid sodium salt dispersed in 30 cc of N,N-dimethyl formamide is slowly pipetted to the 250 cc of washed organometallic coated magnetic particles as described above in Example 4. After milling for 15 minutes, the dispersion is heated for 20 minutes at 100° C. with mixing. The solution, at room temperature, is magnetically separated and washed five times with 1,000 cc of distilled water.

Example 8

SYNTHESIS OF DIHYDROXY AROMATIC TERMINATED MAGNETIC PARTICLES

This example illustrates the preparation of dihydroxyaromatic terminated magnetic particle. 5 g of magnetite coated with titanium isopropoxide and 6-amino-1-hexanol, prepared as above, is dispersed in sodium metabisulfite and distilled water solution, 300 cc. The sodium metabisulfite solution has been pretreated with nitrogen gas to prevent oxidation of the particles. 78 g of gallic acid, and 1.0 g of carboddimide is combined with the amine-terminated magnetic particle with mixing. After incubating for one hour, the product is magnetically separated and water washed.

Example 9

MAGNETIC TRACERS FOR IMMUNO ASSAY I 20A non-magnetic ferrite particles were washed 4 times with water, 3 times with acetone and 3 times with anhydrous methanol by collecting the particles after centrifugation and resuspending the particles by vigorous agitation.

TYZOR (titanium tetra-isopropoxide), dissolved in anhydrous methanol was added to 0.53 g dry of particles at 25 g Ti/9.6 g dry particles. Steel balls were added and the particles were milled in a ball mill for one hour.

The particles were then amine terminated by adding 6-amino-1-hexanol dissolved in anhydrous methanol to the TYZOR coated particles. For every 9.6 g dry particles, 0.088 mol amine was used. This was added to the Tyzor coated particles and milled on the ball mill for 3 ½ hours. The magnetics were tested on a vibrating sample magnetometer. The particles were found to be non-magnetic.

The sample was divided into 4 equal dry parts of 0.13 g each. 1,6 diisocyanato-hexane was added to particles in four concentrations: 0, 0.5, 4, 8 lm 1,6 diiso./0.5 g dry. The particles were milled overnight in the ball mill without using steel balls.

The magnetics were tested again on the VSM. It was determined that the increase in 1,6 diisocyananatohexane resulted in a proportional increase in magnetivity.

Example 10

ENCAPSULATION BY A POLYMER 20A non-magnetic ferrite particles were washed 4 times with water, 5 times with acetone, (collecting with a centrifuge between washes). The acetone slurry is then washed 5 times with hexane. A solvent borne solution of the polymer (e.g., polystyrene, polyurethane, poly(vinyl chloride)) from about 0.1%–10% by weight in an amount equal to about 1:10 to 10:1 particle:polymer ratio is then added. Mixing continues for about 10 minutes in a high shear mixer to allow the crystals to coat uniformly with polymer. Water is then added in a volume equal to about 10–100 times the amount of solvent to flocculate the polymer. The beads are then collected. In the case of polyurethane, it has been found the THF is the solvent of choice.

Example 11

ADDITION OF MONOMER FOLLOWED BY CROSSLINKING

A particle slurry is prepared as in Example 10. Oleic acid is then added to the hexane slurry of particles and mixed in a high shear mixer for about 20 minutes. A volume of acetone is then added, equal to approximately 5 times the amount of hexane to the oleic acid coated particle dispersion, in order to flocculate. The resulting residue is collected and mixed in water in a high shear mixer for about 1 hour to produce oleic acid coated crystal beads. The bead slurry is then exposed to 3-beam generator (Energy sources, Woburn, Mass.), from 1–20 meg Rad for about 0.25–0.5 sec., to crosslink through the unsaturated group.

Example 12

PREPARATION OF SUB 10 NM PARTICLES IN A TWO-SIDED DIALYSIS TANK 2 nm diameter uniform magnetic crystals were prepared by controlled contact of a base solution and iron salt solution across a semipermeable membrane, resulting in an iron oxide crystal precipitate of defined size within a narrow size distribution range. A SPECTRO/POR®5 dialysis membrane (flat sheet) was affixed in a manner as to separate two equal sized chambers of a two sided Dialysis reaction tank. Both sides of the tank were filled with 20 liters of distilled $H_2O$ at 20° C. 12.5 g $FeCl_2$ $4H_2O$ and 20 g $FeCl_3$ were added to one chamber of the tank and stirred until dissolved. 60.6 g NaOH were dissolved in 2 liters of $H_2O$ and added to the solution into the opposite chamber in the tank. Both sides were agitated by a mechanical paddle stirrer for 15 min. After 70–80 hours of contact time, the iron solution and precipitated crystals were removed from the tank and the magnetic crystals were collected by centrifugation and measures by TEM to be 2 nm average diameter.

We claim:

1. A method for preparing inorganic oxides of substantially uniform particle size distribution comprising contacting aqueous solutions of a metal (+2) and metal (+3) inorganic salt and an inorganic base across a porous membrane wherein the membrane contains a plurality of pores which allows for precipitation of substantially monodispersed size inorganic oxide particles on one side of the membrane and the formation of a salt of the corresponding base on a second side of the membrane.

2. The method of claim 1 wherein the particle size diameter is 20, 50, 80 or 100A.

3. The method of claim 1 wherein the inorganic salt is of the formula MY, wherein M is selected from the group consisting of Fe, Co, Ni, Zn, Mn, Mg, Ca, Ba, Sr, Cd, Hg, Al, B, Sc, Ga, V In, and Y is selected from the group consisting of Cl, Br, I, $SO_4$, $NO_3$, $PO_4$.

4. The method of claim 1 wherein the inorganic base is selected from the group consisting of $NH_4OH$, KOH, LiOH, NaOH, CsOH, and RbOH.

5. The method of claim 1 wherein the substantially monodispersed precipitated inorganic oxide particle size is from about 20–1000A in diameter.

6. The method of claim 1 wherein the substantially mono-dispersed precipitated inorganic oxide particle is of the formula $M_3O_4$ wherein M is selected from the group consisting of Fe, Co, Ni, Zn, Mn, Mg, Ca, Ba, Sr, Cd, Hg, Al, B, Sc, Ga, V, In and mixtures thereof.

7. The method of claim 1 wherein the substantially mono-dispersed precipitated inorganic oxide particle is $Fe_3O_4$.

8. The method of claim 1 wherein the size of the precipitated inorganic oxide particle is increased by selecting an inorganic base with a relatively rapid dissociation constant.

9. The method of claim 1 wherein the size of the precipitated inorganic oxide particle is reduced by selection of an inorganic base with a relatively slow dissociation constant.

10. The method of claim 1 wherein the size of the precipitated inorganic oxide particles is controlled by selecting a membrane of different pore size.

11. The method of claim 1 wherein the size of the precipitated inorganic oxide particles is controlled by varying the temperature of the inorganic salt and inorganic base solutions.

12. The method of claim 1 wherein the size of the precipitated particles is controlled by adjusting the concentration of the aqueous inorganic salt solution.

13. The method of claim 12 wherein the concentration of the aqueous inorganic salt solution is about 1–30% wt.

14. The method of claim 1 wherein the size of the precipitated inorganic oxide particles is further controlled by adjusting the concentration of the aqueous inorganic base.

15. The method of claim 14 wherein the concentration of the aqueous solution of inorganic base is about 2–4% wt.

16. The method of claim 1 wherein the aqueous inorganic salt solution and the aqueous inorganic base are allowed to remain in contact across said membrane for a period of about 70–80 hours.

17. The method of claim 1 wherein said membrane is selected from material consisting of cellulose polymer, a fluropolymer, a chlorinated olefin polymer, and a polyamide.

18. The method of claim 1 wherein membranes of different pore size are selected with reference to the membranes' value of molecular weight cut-off.

19. A method for preparing precipitated inorganic oxides of substantially uniform particle size distribution comprising:

a. providing an aqueous solution of an inorganic metal (+2) and metal (+3) salt at a concentration of about 1–3% wt; and b. providing an aqueous solution of an inorganic base at a concentration of about 2–4% wt; and c. contacting said solutions across a porous membrane at about 25° C. for a period of about 4–6 hours to precipitate a substantially mono-dispersed inorganic oxide particle on one side of the membrane and the formation a salt of the corresponding base on a second side of the membrane.

20. A method for determining the concentration of a ligate in solution which comprises:

a. providing a substantially mono-dispersed inorganic oxide particle of claim 1 wherein said particles are non-magnetic;

b. coating said particles with an organo-metallic polymer coating which is adsorbed onto or covalently bound to the particle and which is functionalized to covalently bind to a ligand moiety having specific affinity for the ligate to be measured;

c. covalently binding said ligand moiety to the particle;

d. reacting the product in step (c) with a solution containing the ligate to be measured to form a ligand/ligate magnetic complex;

e. relating the magnetic response of the product in step (d) to the concentration of the ligate causing the complexation.

21. The method of claim 20 wherein the ligand is an antibody.

22. The method of claim 21 wherein the antibody is selected from the group consisting of anti-thyroxine, anti-triiodothyronine, anti-thyroid stimulating hormone, anti-thyroid binding globulin, anti-thyroglobulin, anti-digoxin, anti-cortisol, anti-insulin, anti-theophylline, anti-vitamin B-12, anti-folate, anti-ferritin, anti-human chorionic gonadotropin, anti-follicle stimulating hormone, anti-progesterone, anti-testosterone, anti-estriol, anti-estradiol, anti-prolactin, anti-human placental lactogen, anti-gastrin and anti-human growth hormone antibodies.

23. The method of claim 20 wherein the ligate is selected from the group consisting of hormones, peptides, pharmacological agents, vitamins, cofactors, hematolgical substances, virus antigens, nucleic acids and nucleotides.

24. The method of claim 20 wherein the ligate is thyroxine and the ligand is anti-thyroxine antibody.

25. The method of claim 20 wherein the ligate is theophylline and the ligand is an anti-theophylline anti-body.

26. The method of claim 20 wherein the ligate is vitamin B-12 and the ligand is vitamin B-12 binding protein.

27. The method of claim 20 wherein the ligate is triiodothyronine and the ligand is an anti-triiodothyronine antibody.

28. The method of claim 20 wherein the ligate is a thyroid stimulating hormone and the ligand is an anti-thyroid stimulating hormone anti-body.

29. A method for determining the concentration of a metal in solution which comprises:

a. providing a substantially mono-dispersed inorganic oxide particle produced by the process of claim 1 wherein said particles are non-magnetic;

b. coating said particles with an organo-metallic polymer coating which is adsorbed onto or covalently bound to the particle and which is functionalized to covalently bind to an organic moiety having specific affinity for the metal to be measured;

c. covalently binding said organic moiety to the particle;

d. reacting the product in step (c) with a solution containing the metal to be measured to form a magnetic complex;

e. relating the magnetic response of the product in step (d) to the concentration of the metal causing the complexation.

30. The method of claim 29 wherein the organic moiety having specific affinity for a metal to be measured is 2,3-dihydroxy-benzoic acid.

31. The method of claim 29 wherein the metal to be measured is selected from the group consisting of W and Mo.

32. The method of claim 29 wherein the organic moiety having specific affinity for the metal to be measured is 2,3-dithio-benzoic acid and the metal to be measured is Mo.

33. A method for preparing inorganic oxides of substantially uniform particle size distribution comprising contacting aqueous solutions of an inorganic salt and a metal (+2) and metal (+3) inorganic base across a porous membrane wherein the membrane contains a plurality of pores which allows for precipitation of substantially mono-dispersed size inorganic oxide particles on one side of the membrane and the formation of a salt of the corresponding base on a second side of the membrane, wherein the size of the precipitated inorganic oxide particle is selected by adjusting the dissociation constant of the inorganic base.

34. The method of claim 33 wherein the particle size diameter is 20, 50, 80 or 100A.

35. The method of claim 33 wherein the size range of the substantially monodisperse particles varies within about +/−10% of their average size.

36. The method of claim 33 wherein the inorganic salt is of the formula MY, wherein M is selected from the group consisting of Fe, Co, Ni, Zn, Mn, Mg, Ca, Ba, Sr, Cd, Hg, Al, B, Sc, Ga, V In, and Y is selected from the group consisting of Cl, Br, I, $SO_4$, $N_3$, $PO_4$.

37. The method of claim 33 wherein the inorganic base is selected from the group consisting of $NH_4OH$, KOH, LiOH, NaOH, CsOH, and RbOH.

38. The method of claim 33 wherein the substantially mono-dispersed precipitated inorganic oxide particle size is from about 20–1000A in diameter.

39. The method of claim 33 wherein the substantially mono-dispersed precipitated inorganic oxide particle is of the formula $M_3O_4$ wherein M is selected from the group consisting of Fe, Co, Ni, Zn, Mn, Mg, Ca, Ba, Sr, Cd, Hg, Al, B, Sc, Ga, V, In and mixtures thereof.

40. The method of claim 33 wherein the substantially mono-dispersed precipitated inorganic oxide particle is $Fe_3O_4$.

41. The method of claim 33 wherein the size of the precipitated inorganic oxide particles is controlled by selecting a membrane of different pore size.

42. The method of claim 33 wherein the size of the precipitated inorganic oxide particles is controlled by varying the temperature of the inorganic salt and inorganic base solutions.

43. The method of claim 33 wherein the size of the precipitated particles is controlled by adjusting the concentration of the aqueous inorganic salt solution.

44. The method of claim 43 wherein the concentration of the aqueous inorganic salt solution is about 1–3% wt.

45. The method of claim 33 wherein the size of the precipitated inorganic oxide particles is further controlled by adjusting the concentration of the aqueous inorganic base.

46. The method of claim 45 wherein the concentration of the aqueous solution of inorganic base is about 2–4% wt.

47. The method of claim 33 wherein the aqueous inorganic salt solution and the aqueous inorganic base are allowed to remain in contact across said membrane for a period of about 70–80 hours.

48. The method of claim 33 wherein said membrane is selected from material consisting of cellulose polymer, a fluropolymer, a chlorinated olefin polymer, and a polyamide.

49. The method of claim 33 wherein membranes of different pore size are selected with reference to the membranes' value of molecular weight cut-off.

50. A method for preparing precipitated inorganic oxides of substantially uniform particle size distribution comprising:

a. providing an aqueous solution of an inorganic metal (+2) and metal (+3) salt at a concentration of about 1–3% wt; and b. providing an aqueous solution of an inorganic base at a concentration of about 2–4% wt; and c. contacting said solutions across a porous membrane at about 25° C. for a period of about 4–6 hours to precipitate a substantially mono-dispersed inorganic oxide particle on one side of the membrane and a salt of the corresponding base on a second side of the membrane, wherein the size of the precipitated inorganic oxide particle is selected by adjusting the dissociation constant of the inorganic base.

51. A method for preparing inorganic oxides of substantially uniform particle size distribution comprising contacting aqueous solutions of a metal (+2) and metal (+3) inorganic salt and an inorganic base across a porous membrane wherein the membrane contains a plurality of pores which allows for precipitation of substantially mono-dispersed size inorganic oxide particles on one side of the membrane and precipitation of a salt of the corresponding base on a second side of the membrane, wherein the size of the precipitated inorganic oxide particles is selected by adjusting the temperature of the inorganic salt and inorganic base solutions.

52. The method of claim 51 wherein the particle size diameter is 20, 50, 80 or 100A.

53. The method of claim 51 wherein the size range of the substantially monodisperse particles varies within about +/−10% of their average size.

54. The method of claim 51 wherein the inorganic salt is of the formula MY, wherein M is selected from the group consisting of Fe, Co, Ni, Zn, Mn, Mg, Ca, Ba, Sr, Cd, Hg, Al, B, Sc, Ga, V, In, and Y is selected from the group consisting of Cl, Br, I, $SO_4$, $NO_3$, $PO_4$.

55. The method of claim 51 wherein the inorganic base is selected from the group consisting of $NH_4OH$, KOH, LiOH, NaOH, CsOH, and RbOH.

56. The method of claim 51 wherein the substantially mono-dispersed precipitated inorganic oxide particle size is from about 20–1000A in diameter.

57. The method of claim 51 wherein the substantially mono-dispersed precipitated inorganic oxide particle is of the formula $M_3O_4$ wherein M is selected from the group consisting of Fe, Co, Ni, Zn, Mn, Mg, Ca, Ba, Sr, Cd, Hg, Al, B, Sc, Ga, V, In and mixtures thereof.

58. The method of claim 51 wherein the substantially mono-dispersed precipitated inorganic oxide particle is $Fe_3O_4$.

59. The method of claim 51 wherein the size of the precipitated inorganic oxide particle is increased by selecting an inorganic base with a relatively rapid dissociation constant.

60. The method of claim 51 wherein the size of the precipitated inorganic oxide particle is reduced by selection of an inorganic base with a relatively slow dissociation constant.

61. The method of claim 51 wherein the size of the precipitated inorganic oxide particles is controlled by varying the pore size of the membrane.

62. The method of claim 51 wherein the size of the precipitated particles is controlled by adjusting the concentration of the aqueous inorganic salt solution.

63. The method of claim 62 wherein the concentration of the aqueous inorganic salt solution is about 1–3% wt.

64. The method of claim 51 wherein the size of the precipitated particles is further controlled by adjusting the concentration of the aqueous inorganic base.

65. The method of claim 51 wherein the concentration of the aqueous solution of inorganic base is about 2–4% wt.

66. The method of claim 51 wherein the aqueous inorganic salt solution and the aqueous inorganic base are allowed to remain in contact across said membrane for a period of about 70–80 hours.

67. The method of claim 51 wherein said membrane is selected from material consisting of cellulose polymer, a fluropolymer, a chlorinated olefin polymer, and a polyamide.

68. The method of claim 51 wherein membranes of different pore size are selected with reference to the membranes' value of molecular weight cut-off.

69. A method for preparing precipitated inorganic oxides of substantially uniform particle size distribution comprising:

a. providing an aqueous solution of an inorganic metal (+2) and metal (+3) salt at a concentration of about 1–3% wt; and b. providing an aqueous solution of an inorganic base at a concentration of about 2–4% wt; and c. contacting said solutions across a porous membrane at about 25° C. for a period of about 4–6 hours to precipitate a substantially mono-dispersed inorganic oxide particle on one side of the membrane and a salt of the corresponding base on a second side of the membrane, wherein the size of the precipitated inorganic oxide particle is selected by adjusting the temperature of the inorganic salt and inorganic base solutions.

* * * * *

UNITED STATES PATENT AND TRADEMARK OFFICE
CERTIFICATE OF CORRECTION

PATENT NO. : 5,935,866
DATED : August 10, 1999
INVENTOR(S) : CHAGNON ET AL

It is certified that error appears in the above-identified patent and that said Letters Patent is hereby corrected as shown below:

Claim 13, Col. 15, Line 49, "1-30%" should be - -1-3%- -.

Claim 36, Col. 17, Line 40, "N3" should be - -$NO_3$- -.

Signed and Sealed this

Twenty-fourth Day of October, 2000

Attest:

Q. TODD DICKINSON

Attesting Officer       Director of Patents and Trademarks